(12) United States Patent
Stegmann

(10) Patent No.: US 7,491,395 B2
(45) Date of Patent: Feb. 17, 2009

(54) COMPOSITIONS COMPRISING ANTIGEN-COMPLEXES, METHOD OF MAKING SAME AS WELL AS METHODS OF USING THE ANTIGEN-COMPLEXES FOR VACCINATION

(75) Inventor: Antonius J. H. Stegmann, Katwijk (NL)

(73) Assignee: Bestewil Holding B.V., Amsterdam (NL)

( * ) Notice: Subject to any disclaimer, the term of this patent is extended or adjusted under 35 U.S.C. 154(b) by 119 days.

(21) Appl. No.: 11/128,708

(22) Filed: May 13, 2005

(65) Prior Publication Data

US 2005/0214359 A1    Sep. 29, 2005

Related U.S. Application Data

(63) Continuation of application No. PCT/EP03/13084, filed on Nov. 20, 2003.

(51) Int. Cl.
| | |
|---|---|
| A61K 49/00 | (2006.01) |
| A61K 39/385 | (2006.01) |
| A61K 39/12 | (2006.01) |
| A61K 39/02 | (2006.01) |
| A61K 45/00 | (2006.01) |

(52) U.S. Cl. ............ 424/184.1; 424/9.1; 424/9.2; 424/193.1; 424/204.1; 424/234.1; 424/278.1

(58) Field of Classification Search ............... 424/9.1, 424/9.2, 184.1, 193.1, 204.1, 234.1, 278.1; 516/9
See application file for complete search history.

(56) References Cited

U.S. PATENT DOCUMENTS

| | | | |
|---|---|---|---|
| 4,900,549 A | 2/1990 | De Vries et al. | |
| 5,565,203 A | 10/1996 | Gluck et al. | |
| 5,879,685 A | 3/1999 | Gluck et al. | |
| 6,338,859 B1 | 1/2002 | Leroux et al. | |
| 6,733,985 B1 | 5/2004 | Lee | |
| 2001/0018054 A1 | 8/2001 | Hanna et al. | |
| 2001/0019715 A1 | 9/2001 | Hanna et al. | |
| 2001/0053368 A1 | 12/2001 | Burt et al. | |
| 2003/0113347 A1 | 6/2003 | Cusi et al. | |
| 2004/0156867 A1 | 8/2004 | Burt et al. | |

FOREIGN PATENT DOCUMENTS

| | | |
|---|---|---|
| EP | 0 109 942 | 5/1984 |
| EP | 0 231 039 | 8/1987 |
| EP | 0 180 564 | 5/1988 |
| EP | 0 538 437 | 4/1993 |
| WO | WO 88/08718 | 11/1988 |
| WO | WO 92/19267 | 11/1992 |
| WO | WO 99/13912 | 3/1999 |
| WO | WO 99/27954 | 6/1999 |
| WO | WO 00/70084 | 11/2000 |
| WO | WO 01/47553 | 7/2001 |
| WO | WO 01/60402 | 8/2001 |
| WO | WO 02/00194 | 1/2002 |
| WO | WO 2004/045641 | 6/2004 |

OTHER PUBLICATIONS

PCT International Search Report, PCT/EP03/13084, dated Nov. 25, 2004.
PCT International Preliminary Examination Report, PCT/EP03/13084, dated Apr. 25, 2005.
PCT Written Opinion, PCT/EP03/13084, Jan. 13, 2005.
Partial European Search Report, EP 02102610.9, dated Sep. 8, 2003.
Ando et al., "Preparation of Influenza Virosome Vaccine with Muramyldipeptide Derivative B30-MDP," J. Microencapsulation, 1997, pp. 79-90, vol. 14, No. 1.
Baier et al., "Lipopeptides as Immunoadjuvants and Immunostimulants in Mucosal Immunization," Immunobiology, 2000, pp. 391-405, vol. 201.
Lex et al., "A Synthetic Analogue of *Escherichia coli* Lipoprotein, Tripalmitoyl Pentapeptide, Constitutes a Potent Immune Adjuvant," The Journal of Immunology, Oct. 15, 1986, pp. 2676-2681, vol. 137, No. 8.
Schlecht et al., "Enhancement of Protection against Salmonella Infection in Mice Mediated by a Synthetic Lipopeptide Analogue of Bacterial Lipoprotein in *S. typhimurium* Vaccines," Zentralblatt fur Bakteriology, Oct. 1989, pp. 493-500, vol. 271, No. 4.
Reitermann et al., "Lipopeptide Derivatives of Bacterial Lipoprotein Consitute Potent Immune Adjuvants Combined with or Covalently Coupled to Antigen or Hapten," Biol. Chem., Apr. 1989, pp. 343-352, vol. 370, No. 4.
Huber et al., "Modulation of the Th 1/ Th 2 Bias by Lipopeptide and Saponin Adjuvants in Orally Immunized Mice," Immunobiol., Mar. 2002, pp. 61-73, vol. 205, No. 1.
Erdile et al., "OspA lipoprotein of *Borrelia burgdorferi* is a mucosal immunogen and adjuvant," Vaccine, 1997, pp. 988-996, vol. 15, No. 9.
Bron et al., "Preparation, Properties, and Applications of Reconstituted Influenza Virus Envelopes (Virosomes),"0 Methods in Enzymology, 1993, pp. 313-331, vol. 220.
Encyclopedia of Chemical Technology, Fourth Edition, 1995, pp. 55, vol. 15, John Wiley & Sons, USA.
Encyclopedia of Chemical Technology, Fourth Edition, 1997, pp. 488-491, vol. 23, John Wiley & Sons, USA.

*Primary Examiner*—Rodney P. Swartz
(74) *Attorney, Agent, or Firm*—TraskBritt

(57) ABSTRACT

The present invention provides methods and means for preparing vaccines that are capable of eliciting strong immune responses, especially through intranasal delivery. The invention discloses particles, referred to as "co-micelles," in which antigens are present that interact through hydrophobic interactions with certain specific types of amphiphilic compounds, wherein the amphiphilic compounds have adjuvant activity and wherein the antigens are preferably antigenic surface proteins, such as integral membrane proteins from infectious agents like viruses.

15 Claims, 10 Drawing Sheets

FIG. 1A. Virosome
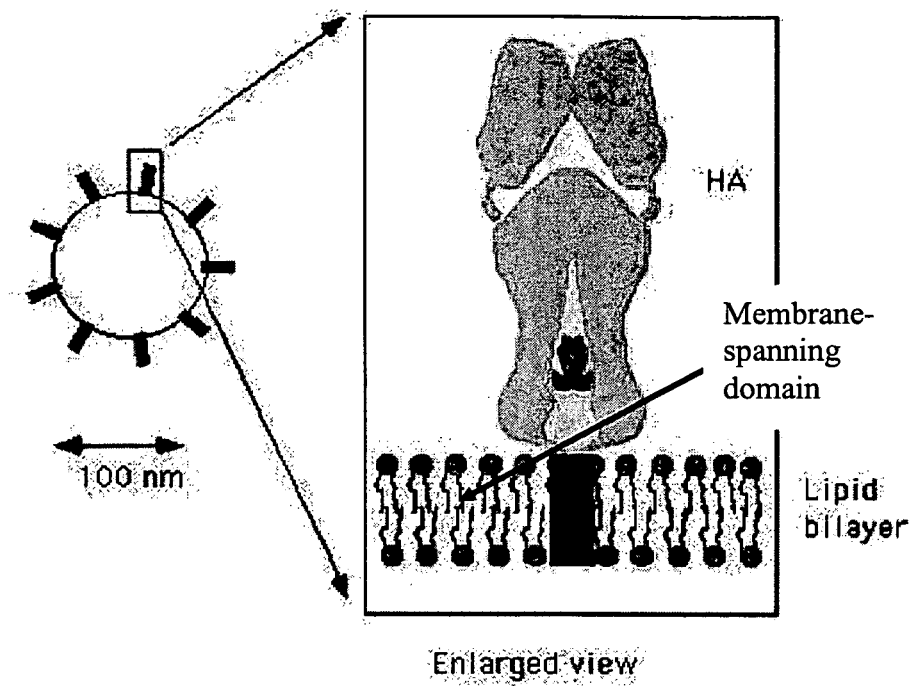
FIG. 1B. co-micelle
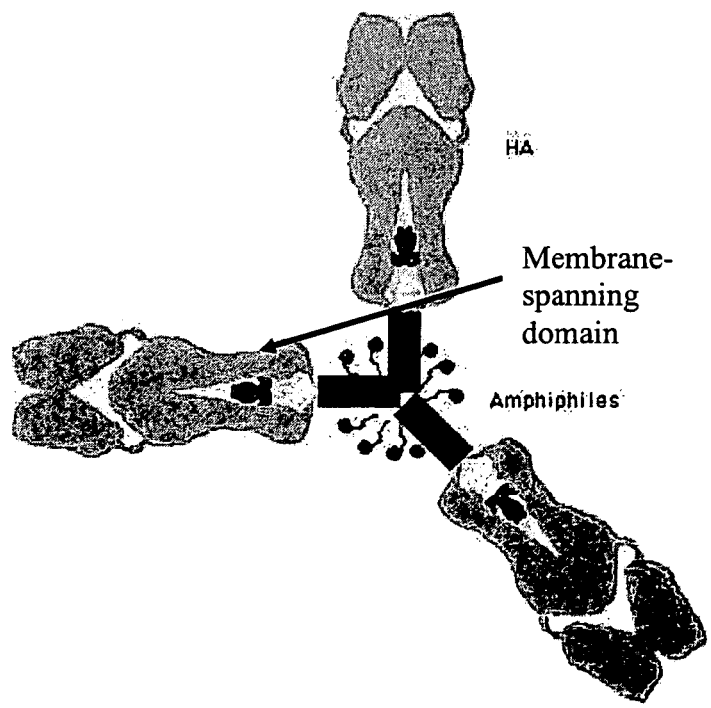

FIG. 5
A
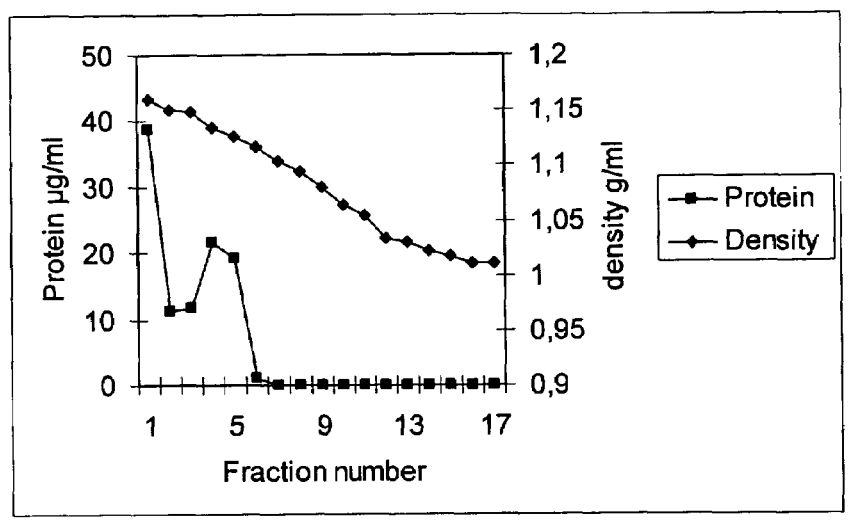
B
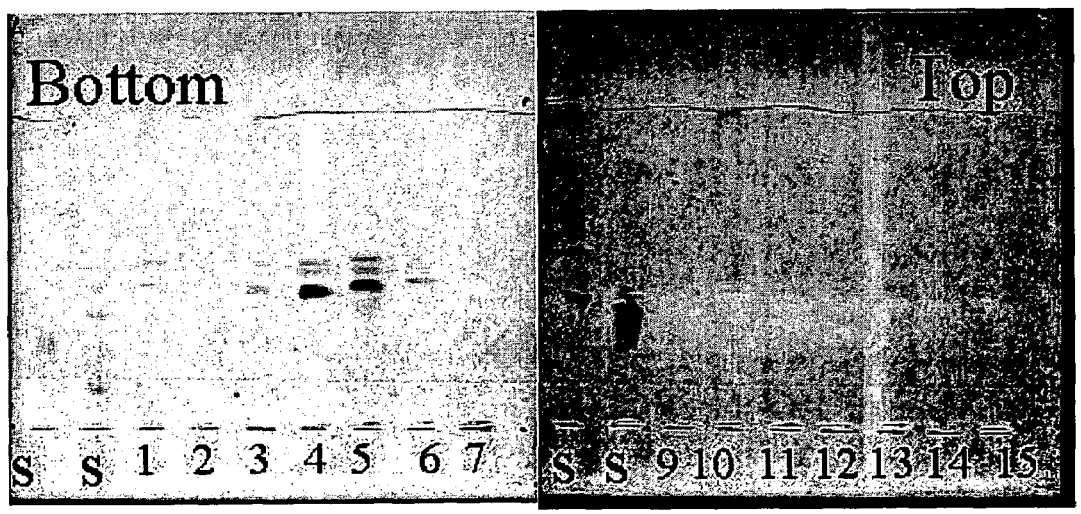
1-15 = Fraction numbers
S = lipopeptide standard

FIG. 7
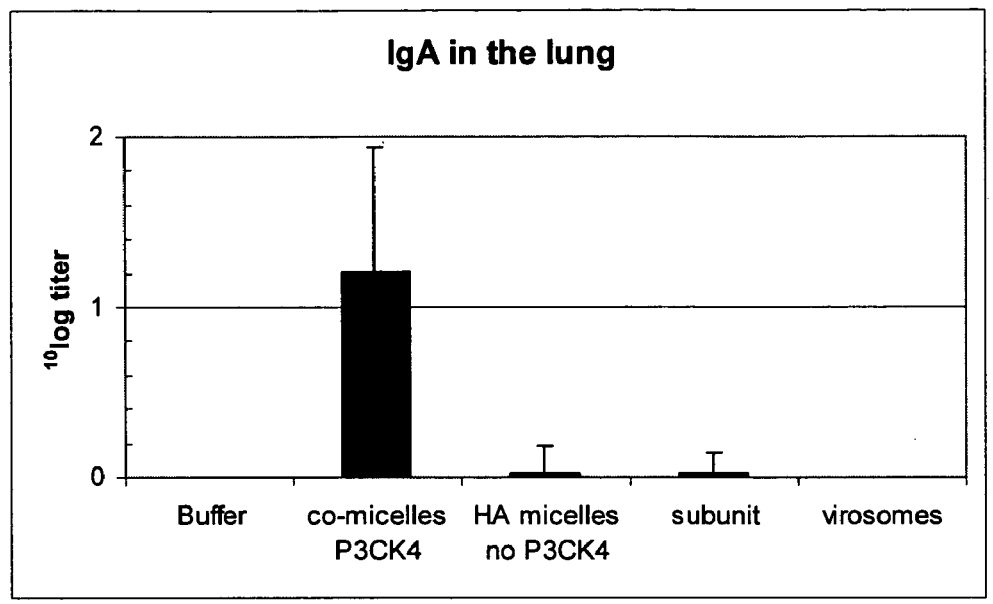
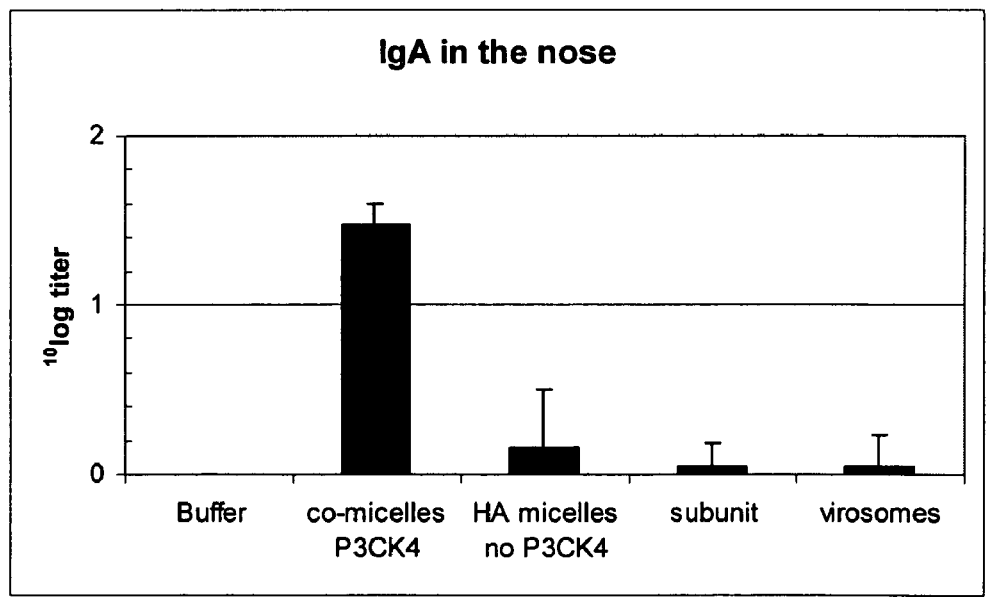

COMPOSITIONS COMPRISING ANTIGEN-COMPLEXES, METHOD OF MAKING SAME AS WELL AS METHODS OF USING THE ANTIGEN-COMPLEXES FOR VACCINATION

CROSS-REFERENCE TO RELATED APPLICATIONS

This application is a continuation of PCT International Patent Application No. PCT/EP2003/013084, filed on Nov. 20, 2003, designating the United States of America, and published in English, as PCT International Publication No. WO 2004/045641 A2 on Jun. 3, 2004, which application claims priority to PCT International Patent Application No. PCT/EP2003/050638, filed Sep. 18, 2003, and to European Patent Application Serial No. 02102610.9 filed Nov. 20, 2002, the entirety of each being incorporated herein by this reference.

TECHNICAL FIELD

The invention relates generally to biotechnology, and, more particularly, to vaccines directed against antigens from pathogens or tumor cells. The invention further relates to methods of forming specific complexes of antigens with amphiphilic compounds and to pharmaceutical compositions comprising such complexes.

BACKGROUND

Classically, vaccines against enveloped viruses either contain killed or live attenuated viruses, or contain their membrane proteins (e.g., split virus preparation). After injection, the virus particles or the proteins are taken up by cells of the immune system (for instance, dendritic cells or macrophages), followed by a presentation of their antigenic parts to effector cells of the immune system. Most vaccines have to be injected to elicit a sufficiently strong immune response because antigen-presenting phagocytes are most abundant just under the skin. However, it has now become clear that such cells are also present in the mucosa that, for instance, lines the nose (Ogra et al. 2001). The phagocytes of the mucosa require much stronger stimulation than those present under the skin (Janeway et al. 2001).

While the injection of some viruses or proteins, for example, influenza virus, elicits an immune response that is sufficiently strong to protect against a later infection by the same virus, this is not the case for many others, for example, respiratory syncytial virus. Numerous attempts to reinforce the immune response by physical or chemical means (by compounds called adjuvants) have been undertaken. The most important principles that emerge from these experiments are as follows. For physical stimulation, it has been found that particles containing multiple copies of viral subunits, such as whole viruses, virosomes, and proteins on microparticle carriers stimulate the immune system better than individual subunits (Ogra et al. 2001; Janeway et al. 2001), whereas chemical stimulation requires that the phagocytes or the effector cells of the immune system receive certain signals through receptors present on the cell surface, for instance, through the use of an adjuvant. With sufficient additional physicochemical stimulation, viral proteins can elicit strong immune responses even if applied to mucous membranes, for example, upon intranasal application (Ogra et al. 2001). Most of the current methods and compositions for stimulating an immune response by such means, whether by chemical or physical means or combinations of the two principles, have significant disadvantages that will be outlined below.

A particular kind of vaccine composition that was developed in the art is known as "virosomes," which are lipid bilayers containing viral glycoproteins (FIG. 1). Virosomes are generally produced by extraction of membrane proteins from viruses with detergents, followed by removal of the detergent in the presence of lipids such that characteristic lipid bilayers are formed with the proteins protruding from them (Stegmann et al. 1987). For some viral antigens, such virosomes elicit protective immune responses that are strong even when the vaccine is delivered through intranasal application (as is exemplified in PCT International Patent Application Publications WO 88/08718 and WO 92/19267). However, 30 to 85% of the viral proteins are lost during the process of virosome formation (WO 88/08718; Stegmann et al. 1987). Moreover, as the insertion of viral protein on either side of the membrane during reconstitution occurs with approximately equal probability, a large part of the protein (one third in the case of the influenza hemagglutinin, Stegmann et al. 1987) present in virosomes is present on the inside of the particles, and thus invisible to the immune system. Also, it is well known in the art that such artificial lipid bilayers render the preparation fragile, causing storage, handling and transport problems. Moreover, optimal formulation often requires complex mixtures of lipids, whose ratio has to be strictly controlled during production. This poses regulatory problems.

The immunogenicity of many viral antigens, for example, influenza hemagglutinin, is only slightly improved with respect to killed viruses when the antigen is presented from virosomes (Gluck et al. 1994). Therefore, to enhance the immune response allowing intranasal application of this vaccine, an adjuvant protein from *Escherichia coli* (heat-labile toxin) was mixed with the virosome influenza vaccine (EP 0538437). Clinical trials indicated that addition of the toxin was necessary to induce serum antibody titers equivalent to injected vaccine (Gluck et al. 1994). Although addition of the toxin did thus enhance the immunogenicity, it also induced a serious side effect known as Bell's Palsy, a temporary paralysis of facial muscles. In this case, the toxin did not form part of the virosomes but was present in the surrounding solution. As the adjuvanting effect of the toxin is due to recognition by an antigen-presenting cell, enhancing its reaction to a viral protein that the cell might take up, and since there is no certainty that the toxin and the viral protein will contact the same cell, a relatively high concentration of the toxin needs to be used in order to ensure activation of every cell. Therefore, clearly, virosomes have promising features, such as their particulate nature, but a fair number of disadvantages.

Alternatively, researchers in the art have also generated antigen complexes different from virosomes, such as "Immunostimulatory Complexes" (ISCOMs, Morein et al. 1984), containing viral proteins complexed with compounds such as Quil A® and saponins (EP 0231039B1; EP 0109942A1; EP 0180564A1), predominantly isolated from the bark of *Quillaia sopanaria Molina*. Mixed with antigen and lipids such as cholesterol, these compounds form cage-like structures of between 30 to 40 nm, rendering the antigen particulate, while acting at the same time as an adjuvant. Although ISCOMs have been used in a number of veterinary vaccines and enhance the immunogenicity of the viral membrane proteins, the development of such vaccines for humans has been inhibited by concerns about their toxicity and the complexity of the mixture (Cox et al. 1998).

More recently, proteosome influenza vaccines were developed (U.S. Pat. No 6,743,900), consisting of non-covalent complexes of the purified outer membrane proteins of bacteria such as meningococci, mixed with antigenic proteins such as the influenza hemagglutinin or the human immunodeficiency envelope glycoprotein. While the presence of these multiple bacterial proteins may act as an adjuvant, the complex nature of such mixtures consisting of multiple proteins will present a regulatory issue.

Another particulate formulation developed by Biovector Therapeutics consists of an inner core of carbohydrate surrounded by a lipid envelope containing antigens. With influenza hemagglutinin as the antigen, some enhancement of the immune response was noted, but not significant enough to warrant further development.

Live attenuated versions of respiratory viruses, such as a cold-adapted strain of influenza virus with minimal replication in the respiratory tract have been developed as intranasal vaccines. These vaccines have the advantage of inducing immune responses that are close to the natural immunity induced by an infection with wild-type virus. For influenza, such vaccines have been known for 20 years and now appear close to commercialization. The delay has been caused by concerns about the ability of many viruses to mutate rapidly, causing the properties of attenuated viruses to revert partially or wholly to wild-type virus and, in fact, causing the disease they were meant to prevent.

For the above reasons, it is well recognized in the art that a need still exists for new vaccine compositions that induce a strong immune response, that do not have the disadvantages of live virus vaccines, that are easily applicable and that have low toxicity. It is, therefore, recognized in the art that there is a need for sub-unit vaccines for intranasal delivery.

SUMMARY OF THE INVENTION

The present invention provides novel means and methods that solve at least part of the problems and difficulties outlined above. The adjuvant activity of certain amphiphilic compounds, such as (synthetic) lipopeptides, is known in the art (Lex et al. 1986; Schlecht et al. 1989; Reitermann et al. 1989; Baier et al. 2000; Huber et al. 2002; Erdile and Guy 1997). Lipopeptides are useful mucosal adjuvants, but have found little practical applicability due to their low water-solubility. Although versions, such as N-palmitoyl-S-2,3(bispalmitoyloxy)-propyl-cysteinyl-seryl-(lysil)$_3$-lysine, have been synthesized with improved water solubility, even these require suspension by ultra-sonication just prior to mixing with the antigen and application to an animal (manufacturer's instructions, EMC Microcollections GmbH). Therefore, as such, these lipopeptides cannot be formulated as part of a commercial vaccine. Integral membrane proteins of pathogens such as viruses are also difficult antigens because they are insoluble in water. Suspensions formed from such proteins ("subunit" vaccines) containing random aggregates of proteins are used in injected vaccines, but the presentation of these proteins to the immune system is so inefficient that they have no activity at all when applied intranasally. The inventor of the present invention has now provided methods and means for making novel compositions referred to as co-micelles that comprise such proteins in a complex with amphiphilic adjuvants such as these lipopeptides and, therefore, has provided new products useful in vaccines against different kinds of disorders and infectious disease, that can be applied via intranasal and/or oral delivery. The invention relates to a co-micelle comprising an amphiphilic compound and an antigen, wherein the amphiphilic compound and the antigen interact through hydrophobic interactions, wherein the amphiphilic compound has adjuvant activity, wherein the antigen is an amphiphilic protein or a fragment thereof, and wherein the hydrophobic parts of the amphiphilic compound and the antigen are directed towards the inside of the co-micelle in an aqueous environment.

The invention further relates to a method for producing a co-micelle, comprising the steps of: i) contacting an amphiphilic compound having adjuvant activity and an antigen solubilized in a solution comprising a detergent; and ii) decreasing the detergent concentration under conditions that cause (or allow) the formation of co-micelles in which the amphiphilic compound and the antigen interact through hydrophobic interactions, wherein the antigen is an amphiphilic protein or a fragment thereof. The invention also relates to co-micelles obtainable by the methods of the invention.

Moreover, the invention provides pharmaceutical preparations comprising co-micelles according to the invention and a therapeutically acceptable carrier, as well as the use of co-micelles or pharmaceutical preparations according to the invention in therapy, prophylaxis or diagnosis, either by intranasal or oral delivery.

DESCRIPTION OF THE FIGURES

FIG. 1 shows a representation of the difference in size and composition between the antigen presenting complexes of the present invention (B) and virosomes (A); virosomes contain a viral integral membrane protein such as the influenza hemagglutinin, in a lipid bilayer, while the antigen presenting complexes of the present invention are co-micelles (not bilayers) of amphiphilic adjuvants with antigens such as the influenza hemagglutinin. In both cases, the membrane-spanning domain of the antigen is present in a hydrophobic environment: the interior of the lipid bilayer in the case of the virosomes and the center of the micelle in the case of the co-micelles of the present invention. Thus, both types of particles expose at least that part of the protein to an aqueous environment, which can elicit an antibody response, and can be recognized on the viral membrane by the generated antibodies.

FIG. 5 consists of a top panel (A) showing the density of fractions of a sucrose gradient, run until equilibrium in an ultracentrifuge, and the protein contents of these fractions, and a lower panel (B) consisting of two ninhydrin-stained thin layer chromatograms of the different fractions from the gradient (and a lipopeptide standard S), showing the physical association of the lipopeptide and the protein in a co-micelle particle.

FIG. 7 shows the geometric mean titers and standard error of the mean for IgA in groups of ten mice that were immunized twice intranasally, with an interval of two weeks between immunizations, with either buffer, co-micelles of A/Panama proteins complexed with N-palmitoyl-S-2,3(bis-palmitoyloxy)-propyl-cysteinyl-seryl-(lysil)$_3$-lysine (abbreviated as P3CK4), micelles of influenza proteins without the lipopeptide (HA micelles no P3CK4), a standard influenza subunit vaccine (monovalent A/Panama), or virosomes prepared from A/Panama virus as described in Stegmann et al. (1987), in nose (lower panel) or lung (upper panel) washes. Samples were taken three weeks after the second immunization. The differences between the titers obtained after vaccination with co-micelles and all other groups are highly significant.

DETAILED DESCRIPTION OF THE INVENTION

Figure 2:
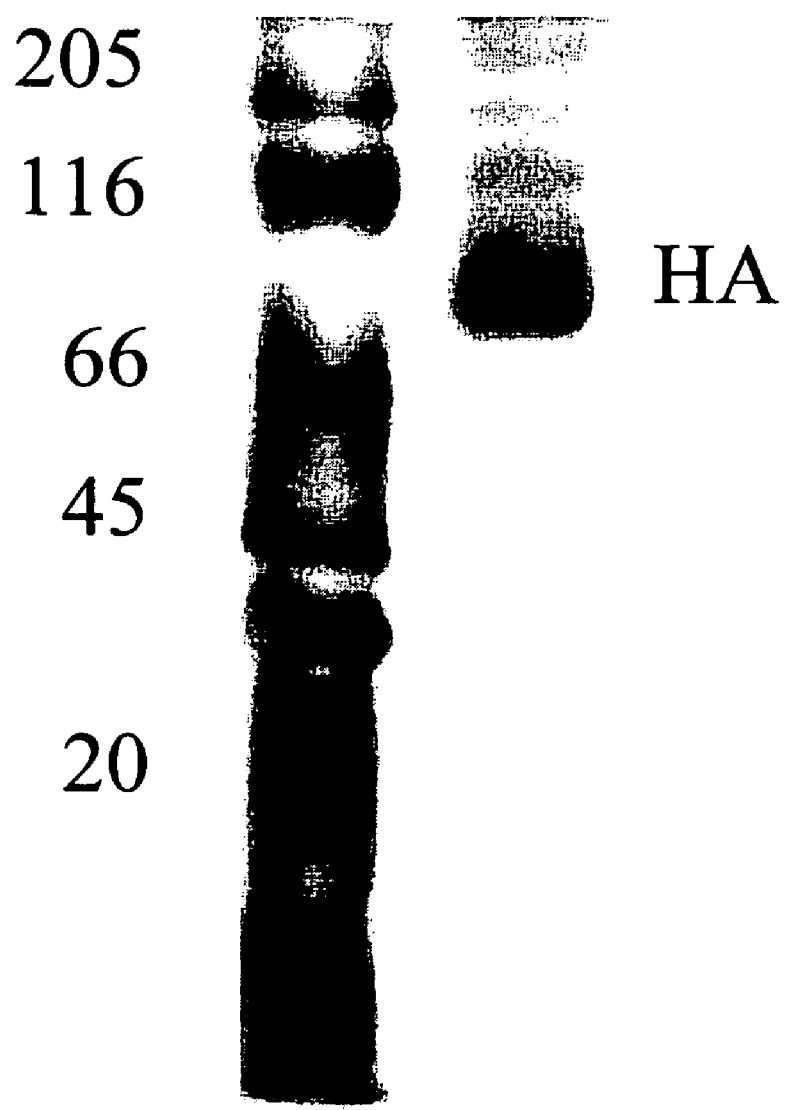
FIG. 2 shows the purification of the hemagglutinin of influenza virus in a silver-stained non-reducing SDS-PAGE gel; left lane, molecular weight standards with their apparent molecular weight in kilodaltons, right lane, purified hemagglutinin.

The present invention relates to methods for producing a co-micelle, the method comprising the steps of: contacting an amphiphilic compound having adjuvant activity and an antigen in a solution comprising a detergent, wherein the antigen is an amphiphilic protein or a fragment thereof; and decreasing the detergent concentration under conditions that cause the formation of co-micelles, in which the amphiphilic compound and the antigen interact through hydrophobic interactions. Preferably, the antigen is an (amphiphilic) membrane protein. Also preferred are surface proteins of infectious agents, such as antigenic surface proteins from viruses. Also preferred is a method according to the invention, wherein the antigen is an amphiphilic outer membrane protein. Highly preferred are methods according to the invention, wherein the antigen comprises an integral membrane protein. In one embodiment, the produced co-micelles are harvested from the solution in a subsequent step. In another embodiment, the antigen is purified before contacting the amphiphilic compound having adjuvant activity. In yet another embodiment, the antigen is de-lipidated (made substantially free of lipids from the membrane the antigen previously interacted with) before contacting the amphiphilic compound having adjuvant activity. De-lipidation is performed to prevent the formation of lipid bilayer membranes. It is to be understood that de-lipidation is never 100%.

The invention also relates to products obtainable by the methods of the present invention. The invention provides co-micelles comprising an amphiphilic compound having adjuvant activity and an antigen, wherein the amphiphilic compound and the antigen interact through hydrophobic interactions, wherein the antigen comprises at least one amphiphilic protein, and wherein the hydrophobic parts of the amphiphilic compound and the antigen are directed towards the inside of the co-micelle in an aqueous environment. Preferably, the antigen present in the co-micelle according to the invention is an (amphiphilic) membrane protein. Also, preferred proteins are surface proteins of infectious agents, such as antigenic membrane proteins of viruses. Preferred is also the co-micelle of the invention, wherein the antigen is an amphiphilic outer membrane protein. Highly preferred are co-micelles according to the invention, wherein the antigen comprises an integral membrane protein.

"Co-micelles," as used herein, refers to micelles formed from at least two different amphiphilic molecules, wherein at least one amphiphilic molecule has adjuvant activity and at least one other amphiphilic molecule (the antigen) is an amphiphilic protein or a fragment thereof. The co-micelle does not comprise a lipid bilayer as in compositions generally referred to as virosomes. Preferably, the co-micelles have a size of between 25 and 42 nm in diameter. In a highly preferred embodiment, the antigen is an integral membrane protein. Integral membrane proteins are generally insoluble in water but can be extracted from a membrane by the action of a detergent or organic solvent, using general methods known to the person of skill in the art. The properties described above distinguish integral membrane proteins from peripheral membrane proteins. Peripheral membrane proteins can be washed from the membrane with brine. Integral membrane proteins are also distinguished from soluble proteins, which are not associated with membranes. Since such integral membrane proteins are very poorly soluble in water, they cannot elicit a strong immune response on their own. The present invention now provides a method for producing novel compositions referred to as co-micelles that comprise such insoluble integral membrane proteins, thereby providing means for producing novel vaccine compositions that are suitable for intranasal and oral delivery.

By "amphiphilic antigens" as used herein, are meant proteins, fragments thereof, stretches of amino acids, peptides or polypeptides that have at least one hydrophilic and at least one hydrophobic moiety and that can elicit an immune response in the host whereto it is delivered. Non-limiting examples of such antigens, preferably integral membrane proteins, are membrane proteins from tumor cells, from bacteria, parasites, yeasts and the envelope of viruses.

"Integral membrane proteins," as used herein, refers to proteins that comprise a hydrophobic domain capable of spanning a lipid bilayer membrane and do so in the organism in which they are present in nature. It is to be understood that "integral" does not solely refer to "full-length"; it also refers to proteins that comprise mutations, deletions, additions, protein-swaps, peptide-swaps, and/or other (post-translational and/or chemically induced) modifications. It is, therefore, to be understood that "integral" refers to proteins or fragments thereof that comprise amphiphilic parts that are generally the fragments of the protein that comprise the membrane-spanning domain or a part thereof. Mutations in the outer (generally antigenic) part of the protein, as well as mutations in the membrane-spanning domain, are encompassed by the claims in the present disclosure, as long as the protein undergoes hydrophobic interactions with the amphiphilic compounds used in the methods and co-micelles of the present invention.

"Amphiphilic compounds," as used herein, refers to compounds that have at least one hydrophobic and at least one hydrophilic moiety and are, therefore, neither completely soluble in water nor in organic solvents.

By "amphiphilic compounds with adjuvant activity," as used herein, are meant naturally occurring, partly synthetic, or synthetic compounds that have at least one hydrophilic and at least one hydrophobic moiety and that are capable of forming a co-micelle with an antigen of interest in an aqueous environment under conditions that allow co-micelle formation. Examples of such amphiphilic compounds are lipopeptides. Preferred lipopeptides are lipopeptides that are recognized by Toll-like receptors (TLRs). Toll-like receptors are transmembrane proteins with leucine-rich repeats that carry structural homology to the Toll protein in *Drosophila* and are activated by a variety of microbial signals from bacteria not normally present in the host. All lipopeptides listed in Table 1 are known to interact with TLRs. Other examples of amphiphilic compounds are glycolipids and peptides that target (bind to) receptors on antigen-presenting cells, such as dendritic cells. Preferably, dendritic cells are targeted by the glycolipids and/or the peptides. In one embodiment of the invention, the amphiphilic compound is derivable from a bacterium, while it is also preferred that the amphiphilic compound is acceptable for use in humans.

"Derivable," as used herein, means that the amphiphilic compound may be directly derived (obtained and/or purified to a certain extent) from (for instance) a bacterium, although it also means that it may be synthetically, biosynthetically, enzymatically produced or otherwise produced or reproduced. This is not critical to the invention. In a preferred aspect of the invention, the amphiphilic compound comprises a lipopeptide. A lipopeptide consists of a peptide covalently bonded to one or more hydrophobic carbohydrate chains, one or more fatty acids, lipids, ceramides, plasmalogens, alkyl or alkene chains, or sterols. Preferred lipopeptides that can be used for the production of co-micelles according to the invention are listed in Table 1. Highly preferred is the lipopeptide N-palmitoyl-S-2,3(bispalmitoyloxy)-propyl-cysteinyl-seryl-(lysil)$_3$-lysine.

In another embodiment of the invention, the amphiphilic compound comprises a glycolipid. Glycolipids are lipids covalently bonded to one or more sugars. Examples are phosphatidyl inositol mannoside, alpha-galactosylceramide or a derivative of either one. As "derivatives" of alpha-galactosyl-ceramide that are useful in co-micelles according to the present invention are to be understood also all derivatives as disclosed in U.S. Pat. No. 5,936,076 having adjuvant activity.

In a preferred embodiment, the amphiphilic compound present in the co-micelle is pharmaceutically acceptable for use in humans. The person skilled in the art would recognize an amphiphilic compound as being acceptable for use in humans. Such compounds should be non-toxic or at least relatively well tolerated and eliciting a significant effect in humans. Adjuvants are substances that, in combination with an antigen, stimulate the immune system, thereby provoking, enhancing or facilitating the immune response. Because the amphiphilic compounds of the invention are not covalently linked, processing of the antigen and presentation of its epitopes to the immune system is, in essence, identical to that of the natural protein alone, ensuring good recognition of the protein present on the natural pathogen.

In another aspect of the present invention, the amphiphilic compound present in the co-micelle according to the invention, comprises a peptide, preferably comprising the sequence of the notch ligand jagged-1 (Weijzen et al. 2002), while in another embodiment, the peptides comprise parts of the *Staphylococcus Aureus* protein A.

An important aspect of the present invention is that the co-micelles of the present invention can be applied for intranasal delivery of antigens that would not normally elicit a sufficient immune response in the treated subject to protect against subsequent infection by the pathogenic organism comprising the antigen. The antigens that are part of the co-micelle according to the invention should have a hydrophobic part that is directed towards the inside of the co-micelle particle. Many pathogenic entities such as viruses, bacteria, yeasts and parasites contain such proteins, for example, in their membrane (also called envelope in the case of viruses) or cell wall. Examples of antigens that have hydrophobic elements and that are suited to be part of the co-micelle of the invention are the integral membrane proteins of enveloped viruses. In preferred embodiments, the antigen is derived from a virus, a parasite or a bacterium. Especially preferred are co-micelles, wherein the antigen is derived from influenza virus. Proteins from influenza virus that can be used in co-micelles of the present invention are preferably the hemagglutinin (HA) protein, the neuramimidase (NA) protein and/or the M2 protein, alone or in combination. A preferred combination comprises HA and NA protein present in a single preparation of co-micelles according to the present invention.

Antigens that can be applied and used in the formation of the co-micelles according to the invention can be derived from all sorts of viruses from different virus families. Non-limiting examples of such families are: Retroviridae, Adenoviridae, Paramyxoviridae, Flaviviridae, Herpesviridae, Bunyaviridae; Hantaviridae, Papovaviridae, Rhabdoviridae, Coronaviridae, Alphaviridae, Arteriviridae, Filoviridae, Arenaviridae and Poxyiridae. Non-limiting examples of viruses from these families that can be used for preparing compositions of the present invention are: Human Immunodeficiency virus (HIV), FIV, SIV, rubella virus, parainfluenza virus, several adenovirus serotypes, measles virus, mumps virus, respiratory syncytial virus, human metapneumovirus, yellow fever virus, dengue virus, Hepatitis C Virus (HCV), Japanese encephalitis virus (JEV), tick-borne encephalitis virus, St. Louis encephalitis virus, West Nile virus, Herpes Simplex virus, cytomegalovirus, Epstein-Barr virus, Hanta virus, human Papillomavirus, rabies virus, human coronavirus (including, but not limited to, a SARS-causing coronavirus), Sindbis virus, Semliki Forest virus, Ebolavirus, smallpox virus and African swine fever virus.

The invention further relates to the use of the co-micelle of the invention for the preparation of a medicament for the prophylactic treatment of a viral-induced disease, such as flu.

Although vaccination is generally applied for the prophylactic protection against pathogens or for the treatment of diseases following pathogenic infection, the person skilled in the art is also aware of the application of some vaccines for tumor-treatment. Moreover, an increasing number of tumor-specific proteins are found to be proper entities that can be targeted by human or humanized antibodies. Such tumor-specific proteins are also within the scope of the present invention. Many tumor-specific antigens are known in the art. Therefore, in one preferred embodiment, the present invention provides co-micelles comprising a tumor-specific antigen. The invention, therefore, also relates to the use of the co-micelle of the invention for the preparation of a medicament for the treatment of a tumor-related disease, such as cancer.

In one aspect, the present invention provides a method for producing a co-micelle, comprising the steps of: contacting an amphiphilic compound having adjuvant activity and an antigen in a solution comprising a detergent; and decreasing the detergent concentration under conditions that allow (or cause) the formation of co-micelles, wherein the amphiphilic compound and the antigen, present in the co-micelle, interact through hydrophobic interactions. Preferably, the method for producing a co-micelle disclosed by the present invention comprises the step of purifying the co-micelle. Adjuvants are substances that, in combination with an antigen, stimulate the immune system, thereby provoking, enhancing or facilitating the immune response. Detergents are amphiphilic molecules with surface activity.

The present invention provides a pharmaceutical preparation comprising the co-micelle of the invention, and a therapeutically acceptable carrier. Therapeutically acceptable carriers for intranasal delivery are substances that are not toxic, or at least known to be tolerated, when applied to the nose. Therapeutically acceptable carriers for intranasal delivery are, for instance, water, buffered saline solutions, glycerin, polysorbate 20, cremophor EL, inulin, cyclodextrins, ethanolamine, glycine, and an aqueous mixture of caprylic/capric glyceride. Since a number of known medicaments in the art are applied intranasally, it is known to the person skilled in the art how such intranasal applications take place, for instance, via injection or sprays.

Furthermore, the present invention relates to the use of the co-micelle of the invention, or a pharmaceutical preparation according to the invention, in therapy, prophylaxis or diagnosis, and/or for the use of the co-micelle of the invention for the preparation of a medicament for the treatment and/or the prevention of a disease caused by an infectious agent, such as influenza virus or any virus as mentioned herein. Preferably, the pharmaceutical preparation according to the invention is used for intranasal delivery. In another embodiment, the pharmaceutical preparation according to the invention may be used for oral or parenteral delivery.

The present invention provides antigen-presenting complexes, herein referred to as co-micelles, that, by definition, do not contain a lipid bilayer and that preferably comprise substantially de-lipidated integral membrane proteins as antigenic determinant mixed with amphiphilic compounds that have adjuvant activity. Such integral membrane proteins are not by themselves soluble in water and have to be extracted from membranes using a detergent or organic solvent. Important, but not limiting, examples of the amphiphilic compounds are glycolipids, lipopeptides and (amphiphilic) peptides. The amphiphilic compounds that are used in the co-micelles of the present invention should be therapeutically acceptable for use in humans, in contrast to, for instance, QUIL A® or saponins that are amphiphils that have been tested in certain settings in the art. The proteins in the co-micelles of the present invention are oriented in the same way as they appear on the viral or cellular membrane, but may present epitopes that are normally partially or at least temporarily hidden when present in a membrane lipid bilayer. Stimulation of the immune system by these antigen-presenting complexes may be due to a combination of their specific recognition by cells of the immune system, their particular character, the presentation of the protein, and the uncovering of hidden epitopes.

EXAMPLES

Example 1

Production of a Lipopeptide-Influenza Membrane Protein Co-Micelle

Influenza virus was produced by growing virus acquired from the World Influenza Center in embryonated eggs, purified by differential ultra-centrifugation, and inactivated by formaldehyde treatment according to established standard procedures known by persons skilled in the art.

The purified and concentrated virus was incubated with a suitable detergent, such as beta-D-octylglucoside (Boehringer Mannheim, Del.) at a concentration of 60 mM (a concentration above the detergent's critical micelle concentration is required) for 30 minutes at 4° C., in an isotonic buffer at neutral pH: 145 mM NaCl, 2.5 mM HEPES, pH 7.4 (Buffer A). The viral nucleocapsid and matrix protein were then removed by centrifugation at 100,000×g for 40 minutes at 4° C. The pellet was discarded and the supernatant was used for purification of viral glycoproteins by passing the supernatant over an affinity chromatography column containing *Ricinis communis* lectin coupled to Sepharose beads (Sigma). The column was washed with five volumes of buffer A containing 30 mM beta-D-octylglucoside to remove the viral lipids. HA was eluted with buffer A containing 0.2 M D(+) galactose and 30 mM beta-D-octylglucoside, followed by pooling the fractions containing HA.

Using this procedure, no proteins other than HA were detected on gel (FIG. 2), indicating that HA was substantially pure. No detectable lipids remained, as determined by the Böttcher procedure, with nanomolar sensitivity (Böttcher et al. 1961). N-palmitoyl-S-2,3(bispalmitoyloxy)-propyl-cysteinyl-seryl-(lysil)$_3$-lysine was suspended in buffer A containing 30 mM beta-D-octylglucoside and mixed at a weight ratio of lipopeptide to protein of 1:1, with the solution containing the membrane glycoprotein (for instance HA from influenza), that was purified as described above, and then the detergent was removed by extensive dialysis. Other useful lipopeptides, next to the N-palmitoyl-S-2,3(bispalmitoyloxy)-propyl-cysteinyl-seryl-(lysil)$_3$-lysine applied above and that can be used for the production of co-micelles according to the invention, are presented in Table 1.

Dialysis or ultra-filtration was carried out using membranes with a cut-off of 30 kD in buffer A, using methods known to the skilled person. The rate of detergent removal was carefully controlled to prevent aggregation and removal of detergent by dialysis was done against 1000 volumes of buffer A for 24 hours at 4° C., with three changes of buffer.

Example 2

Purification and De-Lipidation of the Influenza Membrane Glycoproteins on a DEAE Column Formaldehyde-inactivated influenza virus was produced as in Example 1. The purified virus was concentrated by ultracentrifugation and the viral pellet was resuspended with beta-D-octylglucoside (Boehringer Mannheim, Del.) at a concentration of 60 mM for 30 minutes at 4° C. in a low-salt buffer: 10 mM TRIS, 1 mM EDTA, pH 7.4 (Buffer A). The viral nucleocapsid and matrix protein were then removed by centrifugation at 100,000×g for 35 minutes at 4° C. The pellet was discarded, and the supernatant used for purification of viral glycoproteins.

The viral glycoproteins, mainly hemagglutinin (HA) and neuraminadase (NA), present in the supernatant containing the solubilized viral membrane, were then de-lipidated by application of the sample to a DEAE cellulose ion exchange column (Servacel, DEAE-GS, analytical grade cellulose ion exchanger: 1 ml packed column volume was used per 0.3 mg of viral membrane protein), equilibrated in buffer A, and the column washed with ten column volumes of buffer A.

The following steps are dependent on the virus strain: for the (formaldehyde-inactivated) A/Panama strain, this wash was followed by five volumes of buffer B: 0.1 M NaCl, 10 mM TRIS, 1 mM EDTA, 30 mM octylglucoside, pH 7.4, resulting in the removal of the 96% of viral membrane lipids. The viral membrane proteins were harvested by elution with five volumes of buffer C: 1 M NaCl, 10 mM TRIS, 1 mM EDTA, 30 mM octylglucoside, pH 7.4.

Figure 3:
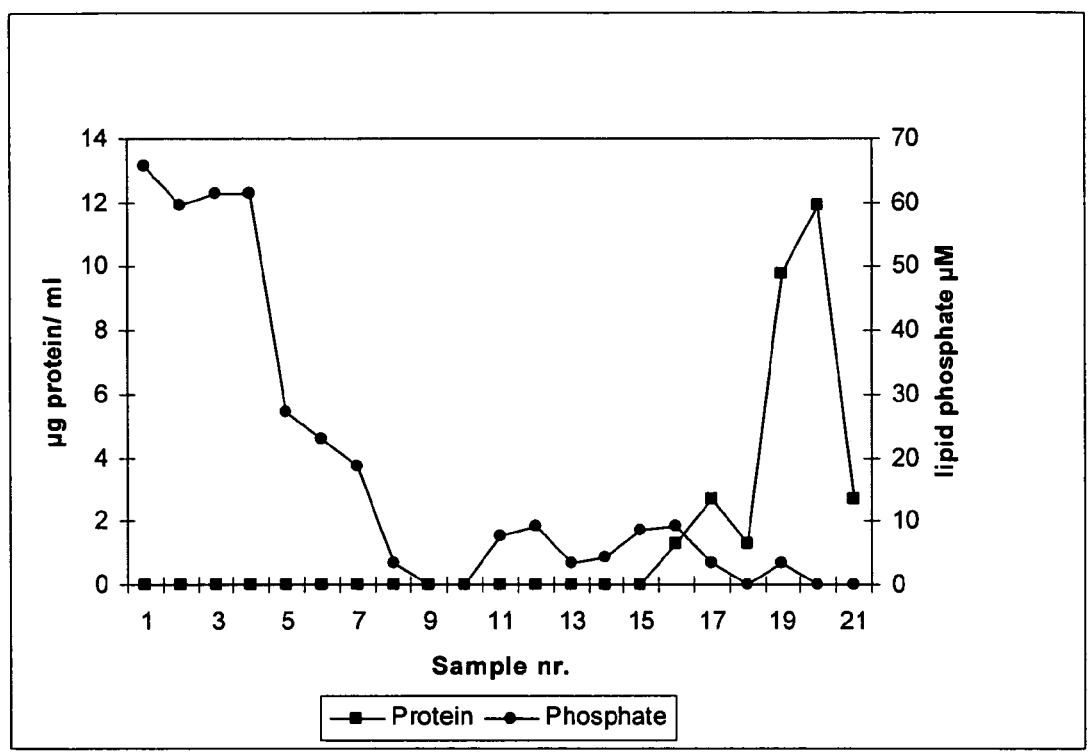
FIG. 3 shows the de-lipidation of influenza A/new Caledonia 20/99 membrane proteins on a DEAE column; samples 1 to 10 buffer A, 11 to 15, buffer D, 15 to 20 buffer C. Indicated are phospholipid phosphate and protein concentrations in the samples; samples 19 and 20 are pooled and used to produce the co-micelles of Example 2.

For the (formaldehyde-inactivated) A/New Caledonia strain, the wash with buffer A was followed by five volumes of buffer D: 0.05 M NaCl, 10 mM TRIS, 1 mM EDTA, 30 mM octylglucoside, pH 7.4, resulting in the removal of the 98% of viral membrane lipids (FIG. 3). The viral membrane proteins were harvested by elution with five volumes of buffer C: 1 M NaCl, 10 mM TRIS, 1 mM EDTA, 30 mM octylglucoside, pH 7.4 (FIG. 3).

For the (formaldehyde-inactivated) B/Shangdong strain, after the wash with buffer A, the proteins were eluted by adding five volumes of buffer E: 0.05 M NaCl, 10 mM TRIS, 1 mM EDTA, 30 mM octylglucoside, pH 7.4, resulting in the removal of the 96% of viral membrane lipids.

Example 3

Production of N-palmitoyl-S-2,3(bispalmitoyloxy)-propyl-cysteinyl-seryl-(lysil)$_3$-Lysine Influenza A/New Caledonia 20/99 Membrane Protein Co-Micelles and Physicochemical Characterization of Co-Micelle Formation The following steps are independent of the virus strain used. N-palmitoyl-S-2,3(bispalmitoyloxy)-propyl-cysteinyl-seryl-(lysil)$_3$-lysine, suspended in buffer A, containing 60 mM beta-D-octylglucoside, was added to the membrane proteins, purified as in example 2, typically at a ratio of 1 mg of proteins per mg of lipopeptide. Subsequently, the detergent was removed by extensive dialysis or ultrafiltration against a buffer isotonic with human physiological conditions at neutral pH: 145 mM NaCl, 2.5 mM HEPES, pH 7.4 (buffer F). Dialysis was carried out using a Slide-a-Lyzer (Pierce). The rate of detergent removal was carefully controlled to prevent aggregation, which could be followed by visual inspection, and typically required dialysis at a ratio of less than 1000 volumes of buffer F until the onset of co-micelle formation. After that, removal of residual detergent required dialysis against at least 1000 volumes of buffer F for at least 24 hours at 4° C. Formation of co-micelles was monitored by spectrometry; at the onset of co-micelle formation, there was a sudden increase in absorbance at 450 nm.

Figure 4:
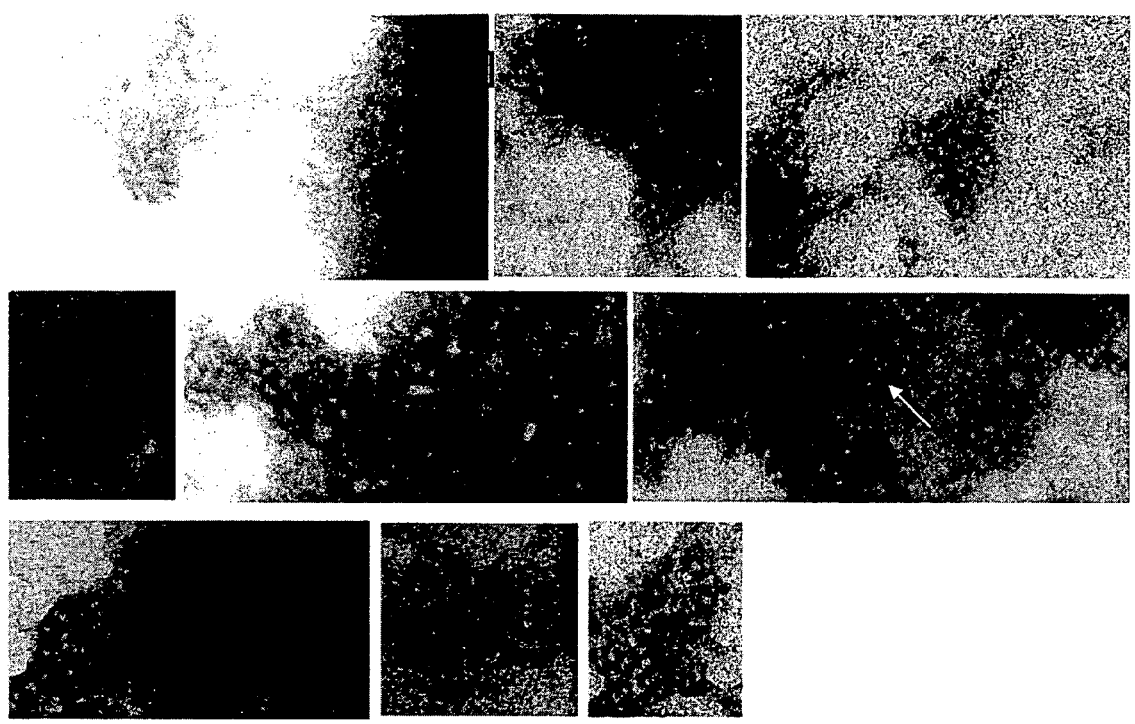
FIG. 4 is a composition of electron micrographs of samples of co-micelles formed from influenza A/New Caledonia and N-palmitoyl-S-2,3(bispalmitoyloxy)-propyl-cysteinyl-seryl-(lysil)$_3$-lysine, at a 1:1 weight ratio, stained with phosphotungsten acid (1% aqueous solution); clearly visible are the hemagglutinin proteins (spikes) protruding from a central core of lipopeptides. In several cases, the influenza hemagglutinin protein projects towards the viewer, allowing the triangular ectodomain to be distinguished, and indicating the central location of the membrane-spanning domain (example of triangular domains indicated by an arrow; the co-micelle that these domains are projecting from is below the plane of focus).

The presence of co-micelles after dialysis was demonstrated by negative stain electron microscopy, using methods known in the art; the complexes were 20 to 40 nm in diameter and show multiple hemagglutinin spikes around a central core, which was most likely formed by the lipopeptides (FIG. 4). Micelles formed by dialysis of purified proteins alone, in the absence of lipopeptide, showed spikes, but lacked the central core.

Figure 6:
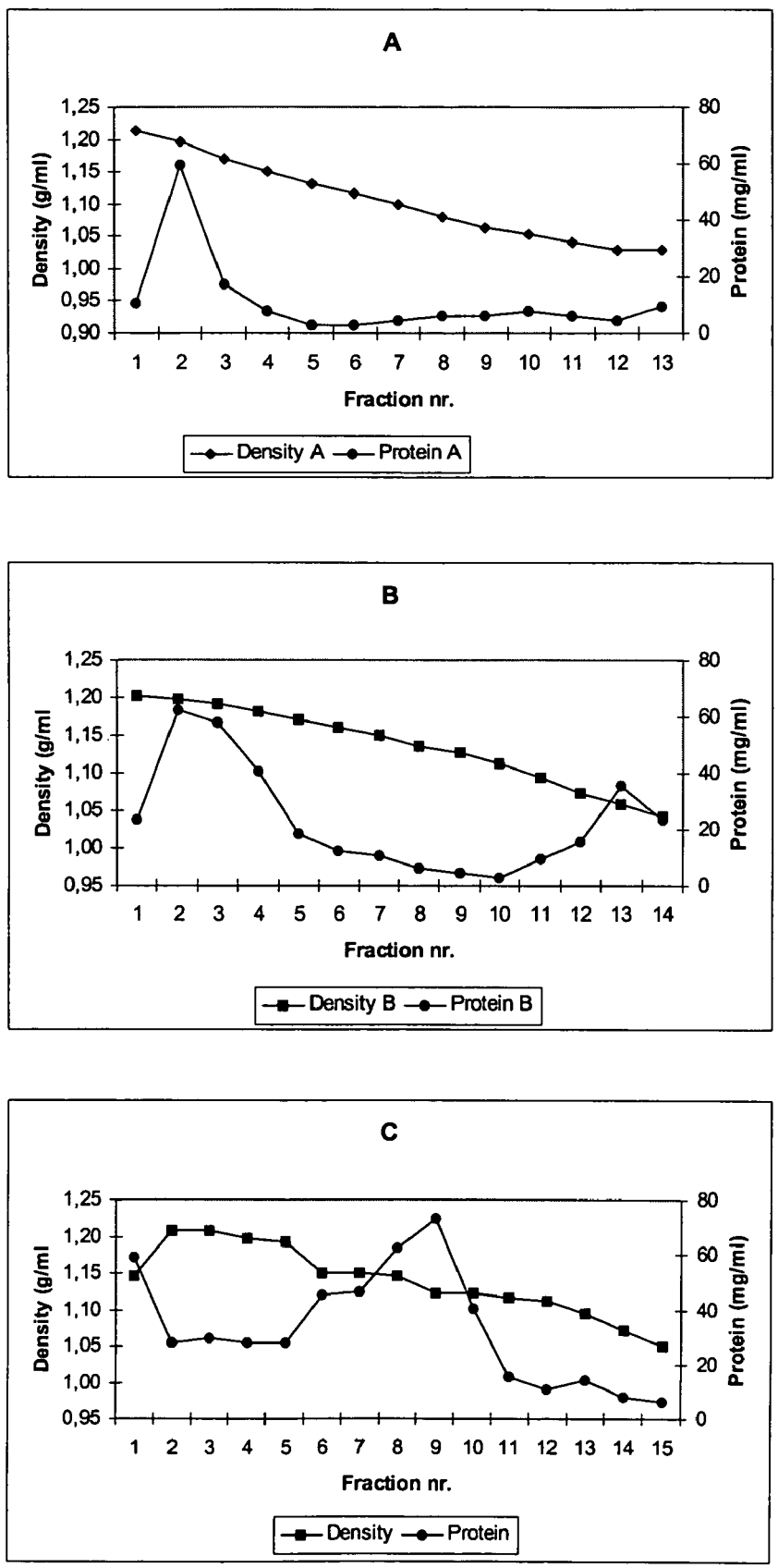
FIG. 6 shows the protein concentration and density of fractions from sucrose gradients such as in FIG. 4, for different protein to lipopeptide ratios: panel (A) at a 14:1, panel (B) 3:1, panel (C) 1:2; notice the presence of non-incorporated viral protein in fraction 1 in panel (C).

The physical association of the proteins and lipopeptide in co-micelles was demonstrated by equilibrium density gradient ultracentrifugation on continuous 10 to 40% sucrose gradients in buffer D. At a 1:1 weight ratio of protein to lipopeptide, a peak containing 50% of the protein and all of the lipopeptide, with a density of 1.122-1.135 g/ml was observed (FIG. 5). More protein remained unincorporated at higher protein-to-lipopeptide ratios, while the density of the co-micelles varies with the protein-to-lipopeptide ratio (FIG. 6): at a 14:1 weight ratio of protein to lipopeptide, the density of the particles was 1.197 g/ml (FIG. 6, panel A); at a 3:1 ratio, there was a broad peak between 1.181 and 1.197 g/ml (Panel B); and at a 1:2 ratio, it was 1.122 g/ml (Panel C). The presence of the lipopeptide was measured by two-dimensional thin-layer chromatography of chloroform extracts of fractions from the gradient, prepared according to Folch (1957); the silica gel TLC plates were first developed in chlorofomm/methanol/water 65/25/4 and subsequently in N-butanol/acetic acid/water 2/1/1; lipopeptides were stained by spraying with a butanolic suspension of ninhydrin 0.1% W/V, developing at 60° C., and quantitated by measuring the intensity of the purple color that was developed (FIG. 5). In all cases, the lipopeptides were present in the fractions that contained the bulk of the protein, demonstrating the physical association of lipopeptides and protein and corroborating the results of the electron microscopy.

Example 4

Intranasal Immunization Experiments Using Antigen-Presenting Complexes Prepared from A/Panama Membrane Proteins and N-palmitoyl-S-2,3(bispalmitoyloxy)-propyl-cysteinyl-seryl-(lysil)$_3$-lysine Intranasal immunization with an antigen-presenting complex containing the influenza virus A/Panama hemagglutinin and N-palmitoyl-S-2,3(bispalmitoyloxy)-propyl-cysteinyl-seryl-(lysil)$_3$-lysine, at a 1:1 weight ratio of lipopeptide to protein, was prepared as described above and was compared to intranasal instillation of buffer only, micelles containing hemagglutinin but not the lipopeptide, a standard subunit vaccine, and to virosomes. To prepare micelles without the lipopeptide, a viral membrane protein supernatant was prepared as in Example 2 and then the detergent was removed by dialysis against buffer A, yielding a preparation of HA micelles that is commonly referred to as "HA rosettes" in literature. Virosomes were prepared form A/Panama membranes, as described in Stegmann et al. (1987). Six to eight-week old female Balb/C mice were immunized with a total of 5 µg per mouse by intranasal instillation of 5 µl of antigen into each nostril under isoflurane/NO$_2$ anesthesia, and kept on their back, anesthetized, for 3 to 5 minutes thereafter. In most groups, a booster instillation was given two weeks after the first application. Blood, nasal and lung washes were collected, either two weeks after primary immunization or three weeks after the second. Lung washes were performed by injection of 1 ml of phosphate-buffered saline (PBS) into the lungs via a syringe connected to the trachea, followed by aspiration of the fluid. Nasal washes were collected by aspirating 0.5 ml of PBS retrograde, via the trachea, into the nasopharynx, the lavage fluid being subsequently collected at the nostrils. Protease inhibitor mix (Boehringer) was added to the washes immediately, they were placed on ice, while debris and cellular components were immediately removed from the lavages by centrifugation, and all samples were processed within 24 hours. Blood samples were collected retroorbitally or from the vena cava. Antigen-specific IgA and IgG were measured by ELISA. For this purpose, ELISA plates (Greiner Bio-one) were coated with commercial influenza subunit vaccine (Solvay, 100 μl per well, at a concentration of 0.2 ng per well, overnight at 37° C.) in coating buffer (0.05 M sodium bicarbonate, pH 9.6), washed once with coating buffer, blocked for 45 minutes at 37° C. with 100 μl blocking buffer (2.5% milk powder in coating buffer), and washed once with coating buffer and twice with PBS/0.05% w/v Tween-20.

Serial two-fold dilutions of samples (100 μl per well) were then applied to the plates, and incubated for 90 minutes at 37° C., the plates were washed with PBS/Tween three times, incubated with a 1:5000 dilution of the appropriate goat-anti-mouse Ig coupled to horse radish peroxidase for 60 minutes at 37° C., washed three times with PBS/Tween and once with PBS, after which 100 μl staining solution (containing 20 mg o-phenylenediamine, added from a 2 ml ethanolic solution to 100 ml of 50 mM sodium phosphate buffer at pH 5.6, and 20 μl of $H_2O_2$) was added for 30 minutes at room temperature. The reactions were stopped by adding 50 μl of $H_2SO_4$, 50 μl per well, the absorbance at 492 μm was determined in an ELISA reader, and the titers were calculated as the reciprocal dilutions of sample at which the absorbance reads 0.2 OD units above background.

Figure 8:
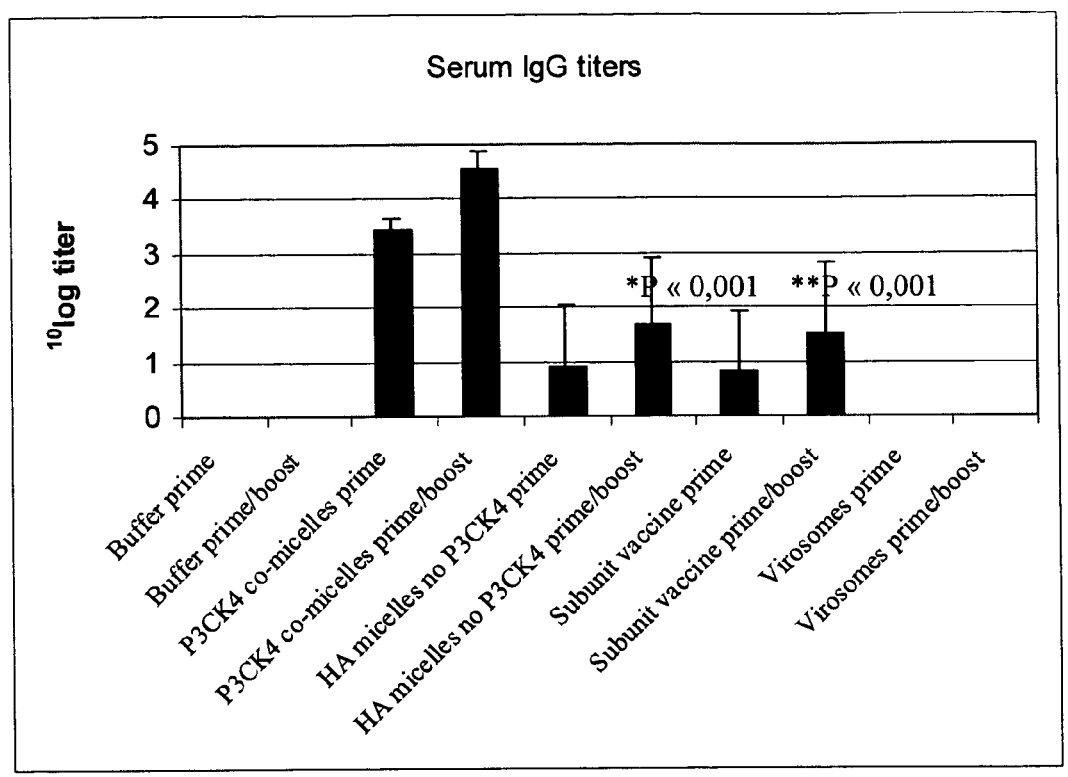
FIG. 8 shows the geometric mean titers and standard error of the mean for serum IgG in groups of ten mice that were immunized intranasally once (prime) or twice (prime/boost) with an interval of two weeks between immunizations, with either buffer, co-micelles of A/Panama proteins complexed with N-palmitoyl-S-2,3(bispalmitoyloxy)-propyl-cysteinyl-seryl-(lysil)$_3$-lysine (abbreviated as P3CK4), micelles of influenza proteins without the lipopeptide (HA micelles no P3CK4), a standard influenza subunit vaccine (monovalent A/Panama), or with virosomes in a prime and in a prime/boost set up. Samples were taken two weeks after the first, or three weeks after the second, immunization. The differences between the titers obtained after vaccination with co-micelles and all other groups are highly significant; for the two groups indicated with asterisks, p was <<0.001 by Student's t-test.

The IgA titers in nose and lung are presented in FIG. 7, while the serum IgG titers are shown in FIG. 8, which clearly show a significant increase of IgA and IgG titers after using the co-micelles of the present invention, as compared to HA micelles without lipopeptide or when using the standard subunit vaccine or when applying virosomes. These results strongly indicate that the co-micelles of the present invention are useful for intranasal applications and elicit a strong immune response in the host.

Example 5

Figure 9:
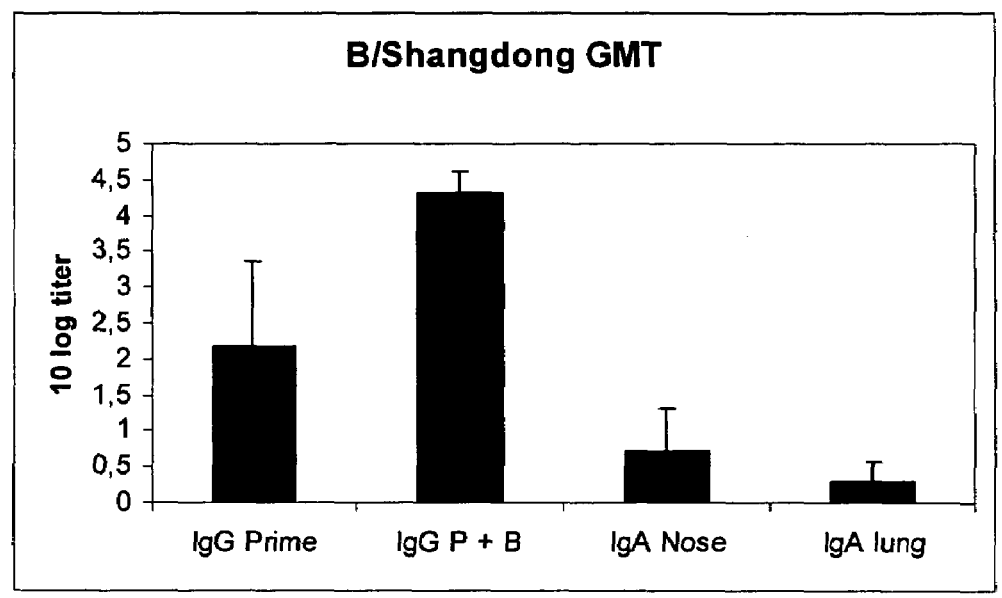
FIG. 9 shows the geometric mean titers (GMT)+standard error of the mean for serum IgG after one (Prime) or two (prime and boost: P+B) intranasal immunizations with co-micelles of B/Shangdong antigenic integral membrane proteins in complex with N-palmitoyl-S-2,3(bispalmitoyloxy)-propyl-cysteinyl-seryl-(lysil)$_3$-lysine. It also shows the nose and lung IgA titers after two immunizations (interval of two weeks between immunizations) in groups of ten mice as described in Example 5. Samples were taken two weeks after the first, or three weeks after the second, immunization.

Intranasal Immunization Experiments Using Antigen-Presenting Complexes Prepared from B/Shangdong Membrane Proteins and N-palmitoyl-S-2,3 (bispalmitoyloxy)-propyl-cysteinyl-seryl-(lysil)₃-lysine Intranasal immunization with antigen-presenting complexes containing the influenza virus B/Shangdong hemagglutinin antigen as the integral membrane protein and N-palmitoyl-S-2,3(bispalmitoyloxy)-propyl-cysteinyl-seryl-(lysil)₃-lysine, at a 1:1 weight ratio of lipopeptide to protein, prepared and characterized as described in Examples 2 and 3, was performed according to the protocol of Example 4. Six to eight-week old female Balb/C mice were immunized with a total of 5 μg per mouse by intranasal instillation of 5 μl of antigen into each nare under isoflurane/NO₂ anesthesia, and kept on their back, anesthetized, for 3 to 5 minutes thereafter. A booster instillation was given two weeks after the first application. Blood was collected at the time of the boost. All blood samples, nasal and lung washes were collected as described in Example 4. Antigen-specific IgA and IgG were measured by ELISA as described in Example 4. Antibody titers are presented in FIG. 9, clearly indicating that the co-micelle composition as used herein was able to elicit a strong IgG and IgA response upon administration, while a prime/boost set-up significantly elevated the IgG titers.

Example 6

Figure 10:
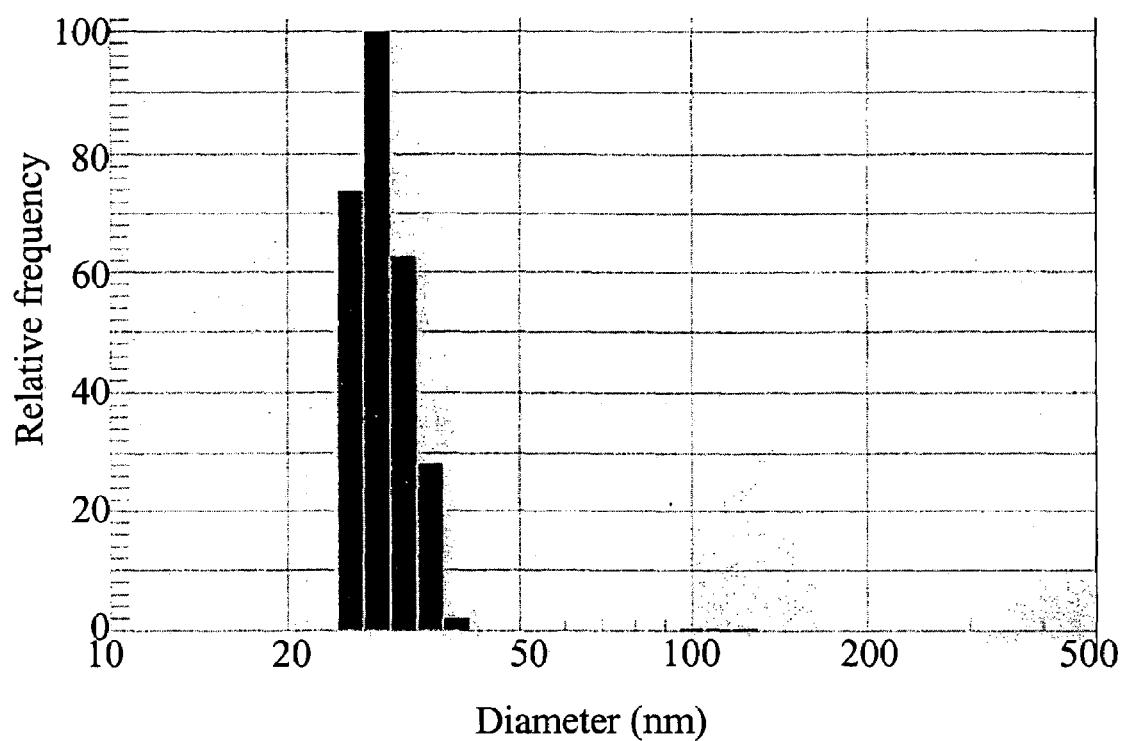
FIG. 10 shows the size distribution of samples of co-micelles according to the present invention formed from antigens from influenza A/New Caledonia in complex with N-palmitoyl-S-2,3(bispalmitoyloxy)-propyl-cysteinyl-seryl-(lysil)$_3$-lysine, at a 1:1 weight ratio, as analyzed in a Nicomp 380 particle size analyzer (Particle Sizing Systems, Inc., Santa Barbara, Calif., USA) using the "solid particle" analysis mode and Nicomp number-weighted distribution analysis.

Size Analysis of Co-Micelles of N-palmitoyl-S-2,3 (bispalmitoyloxy)-propyl-cysteinyl-seryl-(lysil)₃-lysine and Influenza A/New Caledonia 20/99 Membrane Protein The size of the co-micelles, produced as described in Example 3, was analyzed in a Nicomp 380 particle size analyzer (Particle Sizing Systems, Inc., Santa Barbara, Calif., USA) using the "solid particle" analysis mode and Nicomp number-weighted distribution analysis known to persons skilled in the art. The particle size distribution is shown in FIG. 10. 99.5% of the co-micelles were found to be between 25 and 42 nm in diameter, and 0.4% had a size of around 110 nm. The average size of the co-micelles was 29.1 nm.

TABLE 1

Lipopeptides particularly suitable for making co-micelles according to the invention.

N-palmitoyl-S-2,3(bispalmitoyloxy)-propyl-cysteinyl-seryl-serine
S-2,3(bispalmitoyloxy)-propyl-cysteinyl-seryl-serine
N-palmitoyl-S-2,3(bispalmitoyloxy)-propyl-cysteinyl-seryl-(prolyl)₃-proline amide
N-palmitoyl-S-2,3(bispalmitoyloxy)-propyl-cysteinyl-seryl-(histidyl)₃-histidine
N-palmitoyl-S-2,3(bispalmitoyloxy)-propyl-cysteinyl-seryl-(glutamyl)₃-glutaminic acid
N-palmitoyl-S-2,3(bispalmitoyloxy)-propyl-cysteinyl-seryl-(lysil)₃-lysine
N-palmitoyl-S-2,3(bispalmitoyloxy)-propyl-cysteine
S-2,3(bispalmitoyloxy)-propyl-cysteinyl-seryl-(lysil)₃-lysine
N-palmitoyl-S-2,3(bisoleoyloxy)-propyl-cysteinyl-seryl-(lysil)₃-lysine
S-2,3(bisoleoyloxy)-propyl-cysteinyl-seryl--(lysil)₃-lysine
N-palmitoyl-S-2,3(bismyristoyloxy)-propyl-cysteinyl-seryl-(lysil)₃-lysine
S-2,3(bismyristoyloxy)-propyl-cysteinyl-seryl-(lysil)₃-lysine
N-palmitoyl-S-3(palmitoyloxy)-propyl-cysteinyl-seryl-(lysil)₃-lysine
N-palmitoyl-S-2,3 hydroxy-propyl-cysteinyl-seryl-(lysil)₃-lysine

REFERENCES

Baier, W., N. Masihi, M. Huber, P. Hoffmann and W. G. Bessler (2000) *Immunobiology* 201:391-405
Böttcher, C. J. F., C. M. Van Gent and C. J. Fries (1961) *Anal. Chim. Acta.* 24:203-204
Cox, J. C., A. Sjolander and I. G. Barr (1998) *Adv. Drug. Delivery* 32:247-271
Erdile, L. F. and B. Guy (1997) *Vaccine* 15:988-996
Gluck et al. (1994) *J. Infect. Dis.* 181:1129-1132
Huber, M., W. Baier, W. G. Bessler, L. Heinevetter (2002) *Immunobiology* 205:61-73
Janeway et al. (2001) *Immunobiology*, 5th edition, Garland Publishing, New York
Lex et al. (1986) *J. Immunology* 137:2676-2681
Morein et al. (1984) *Nature* 308:457-460
Ogra, P. L., H. Faden and R. C. Welliver (2001) *Clin. Microbiol. Rev.* 14:430-445

Reitermann, A., J. Metzger, K.-H. Wiesmuller, G. Jung and W. G. Bessler (1989) *Biol. Chem.* 370:343-352

Schlecht, S., K.-H. Wiesmuller, G. Jung and W. G. Bessler (1989) *Zbl. Bakt.* 271:493-500

Stegmann, T., H. W. M. Morselt, F. P. Booy, J. F. L. Van Breemen, G. Scherphof and J. Wilschut (1987) *EMBO J.* 6:2651-2659

Weijzen, S., M. P. Velders, A. G. Elmishad, P. E. Bacon, J. R. Panella, B. J. Nickoloff, L. Miele and W. M. Kast (2002) *J. Immunol.* 169:4237-4238

What is claimed is:

1. A method for producing a co-micelle, said method comprising the steps of:
    (i) contacting an amphiphilic compound having adjuvant activity and an antigen in a solution comprising a detergent, wherein said detergent is present in a concentration above the detergent's critical micelle concentration, wherein said antigen comprises an amphiphilic peptide; and
    (ii) decreasing the detergent's concentration under conditions that cause the formation of a co-micelle in which said amphiphilic compound and said antigen interact through hydrophobic interactions.

2. The method according to claim 1, wherein said amphiphilic peptide is a surface protein of an infectious agent.

3. The method according to claim 1, wherein said amphiphilic peptide is a membrane protein.

4. The method according to claim 3, wherein said amphiphilic peptide is an outer membrane protein.

5. The method according to claim 1, wherein said amphiphilic peptide is an integral membrane protein.

6. The method according to claim 1, further comprising: harvesting said co-micelle from the solution.

7. The method according to claim 1, wherein said antigen is purified before contacting said amphiphilic compound.

8. The method according to claim 1, wherein said antigen is de-lipidated before contacting said amphiphilic compound.

9. A co-micelle comprising:
an amphiphilic compound having adjuvant activity, and
an antigen comprising at least one amphiphilic peptide,
wherein the amphiphilic compound and antigen interact through hydrophobic interactions, and wherein the hydrophobic parts of the amphiphilic compound and antigen are directed towards the co-micelle's inside in an aqueous environment and
wherein said amphiphilic compound comprises a lipopeptide, wherein said lipopeptide is selected from the group consisting of: N-palmitoyl-S-2,3(bispalmitoyloxy)-propyl-cysteinyl-seryl-serine, S-2,3(bispalmitoyloxy)-propyl-cysteinyl-seryl-serine, N-palmitoyl-S-2,3bispalmitoyloxy)-propyl-cysteinyl-seryl-(lysil)$_3$-lysine, S-2,3 (bispalmitoyloxy)-propyl-cysteinyl-seryl-(lysil)$_3$-lysine, N-palmitoyl-S-2,3(bisoleoyloxy)-propyl-cysteinyl-seryl-(lysil)$_3$-lysine, S-2,3(bisoleoyloxy)-propyl-cysteinyl-seryl-(lysil)$_3$-lysine, N-palmitoyl-S-2,3(bismyristoyloxy)-propyl-cysteinyl-seryl-(lysil)$_3$-lysine, S-2,3(bismyristoyloxy)-propyl-cysteinyl-seryl-(lysil)$_3$-lysine, N-palmitoyl-S-3(palmitoyloxy)-propyl-cysteinyl-seryl-(lysil)$_3$-lysine, and N-palmitoyl-S-2,3 hydroxy-propyl-cysteinyl-seryl-(lysil)$_3$-lysine.

10. A co-micelle comprising:
an amphiphilic compound having adjuvant activity, and
an antigen comprising at least one amphiphilic peptide,
wherein the amphiphilic compound and antigen interact through hydrophobic interactions, and wherein the hydrophobic parts of the amphiphilic compound and antigen are directed towards the co-micelle's inside in an aqueous environment and
wherein said amphiphilic compound comprises a lipopeptide, wherein said lipopeptide is N-palmitoyl-S-2,3(bispalmitoyloxy)-propyl-cysteinyl-seryl-(lysil)$_3$-lysine.

11. A co-micelle comprising:
an amphiphilic compound having adjuvant activity, and
an antigen comprising at least one amphiphilic peptide,
wherein the amphiphilic compound and antigen interact through hydrophobic interactions, and wherein the hydrophobic parts of the amphiphilic compound and antigen are directed towards the co-micelle's inside in an aqueous environment and
wherein said amphiphilic compound comprises a lipopeptide, wherein said lipopeptide is recognized by a Toll-like receptor.

12. A co-micelle comprising:
an amphiphilic compound having adjuvant activity and
an antigen comprising at least one amphiphilic peptide,
wherein the amphiphilic compound and antigen interact through hydrophobic interactions, and wherein the hydrophobic parts of the amphiphilic compound and antigen are directed towards the co-micelle's inside in an aqueous environment and wherein said amphiphilic compound comprises a glycolipid.

13. The co-micelle of claim 12, wherein said glycolipid comprises phosphatidyl inositol mannoside and/or alpha-galactosylceramide.

14. A purified or isolated co-micelle produced by the method of claim 1, wherein said amphiphilic compound comprises a peptide.

15. A purified or isolated co-micelle produced by the method of claim 1, wherein said amphiphilic compound is a glycolipid and wherein said glycolipid or said peptide binds to a receptor on an antigen presenting cell or a receptor on a dendritic cell.

* * * * *